(12) United States Patent
Becker

(10) Patent No.: US 11,045,214 B2
(45) Date of Patent: *Jun. 29, 2021

(54) INCREASED AXIAL LOAD CARRYING SHEATHED IRRIGATING BALLOON CATHETER

(71) Applicant: Bruce B. Becker, Malibu, CA (US)

(72) Inventor: Bruce B. Becker, Malibu, CA (US)

( * ) Notice: Subject to any disclaimer, the term of this patent is extended or adjusted under 35 U.S.C. 154(b) by 310 days.

This patent is subject to a terminal disclaimer.

(21) Appl. No.: 15/997,586

(22) Filed: Jun. 4, 2018

(65) Prior Publication Data

US 2018/0280041 A1   Oct. 4, 2018

Related U.S. Application Data

(63) Continuation of application No. 14/606,922, filed on Jan. 27, 2015, now Pat. No. 9,987,025, which is a
(Continued)

(51) Int. Cl.
*A61B 17/22* (2006.01)
*A61F 9/007* (2006.01)
(Continued)

(52) U.S. Cl.
CPC .......... *A61B 17/22* (2013.01); *A61B 1/00082* (2013.01); *A61B 1/00135* (2013.01); *A61B 1/00165* (2013.01); *A61B 5/4222* (2013.01); *A61B 17/24* (2013.01); *A61F 9/00772* (2013.01); *A61M 5/007* (2013.01); *A61M 25/1036* (2013.01); *A61M 29/02* (2013.01); *A61B 2017/22051* (2013.01); *A61B 2017/22079* (2013.01); *A61B 2017/246* (2013.01); *A61B 2217/007* (2013.01); *A61M 2210/0612* (2013.01)

(58) Field of Classification Search
CPC ............ A61B 1/00082; A61B 1/00135; A61B 1/00165; A61B 17/24; A61B 2017/22051; A61B 2017/22079; A61B 2017/246; A61B 2217/007; A61M 5/007; A61M 25/1036; A61M 2210/0612; A61F 9/00772
See application file for complete search history.

(56) References Cited

U.S. PATENT DOCUMENTS 4,798,193 A * 1/1989 Giesy ................ A61M 25/0105
600/114
2003/0191435 A1 * 10/2003 Shkolnik ........... A61M 25/1034
604/103
(Continued)

*Primary Examiner* — Adam Marcetich

(57) ABSTRACT

A sheathed tubular semi-rigid balloon catheter for performing probing, irrigation, dilation, suction and potential intubation of the nasolacrimal system or paranasal sinus system to treat for stenosis or obstruction. The catheter includes a sheathed tubular probe portion through which a tracer fluid can be injected and through which suctioning of blood or other material can be conducted. The sheath portion of the device can have a distal segment that is inflated in order to dilate parts the nasolacrimal or paranasal sinus system. The high axial load accommodating catheter tool includes a more secure and inexpensively manufactured bond between the metallic semi-rigid tube of the probe portion and the plastic hand-manipulable, multi-connector hub using an enlarged bonding collar.

18 Claims, 10 Drawing Sheets

Related U.S. Application Data continuation-in-part of application No. 14/520,052, filed on Oct. 21, 2014, now Pat. No. 9,700,706.

(51) Int. Cl.
| | | |
|---|---|---|
| *A61M 29/02* | (2006.01) | |
| *A61B 1/00* | (2006.01) | |
| *A61B 5/00* | (2006.01) | |
| *A61B 17/24* | (2006.01) | |
| *A61M 5/00* | (2006.01) | |
| *A61M 25/10* | (2013.01) | |

(56) References Cited

U.S. PATENT DOCUMENTS

| | | | |
|---|---|---|---|
| 2005/0059958 A1* | 3/2005 | Lessard | A61M 25/0009 604/533 |
| 2007/0010847 A1* | 1/2007 | Pepper | A61M 25/0043 606/194 |
| 2008/0287908 A1* | 11/2008 | Muni | A61B 17/24 604/506 |
| 2011/0178427 A1* | 7/2011 | Tan | A61B 5/1438 600/578 |
| 2013/0072958 A1* | 3/2013 | Ressemann | A61B 1/06 606/199 |
| 2013/0123833 A1* | 5/2013 | Lesch | A61M 29/02 606/196 |
| 2014/0052066 A1* | 2/2014 | Dangoisse | A61B 5/150519 604/168.01 |

* cited by examiner

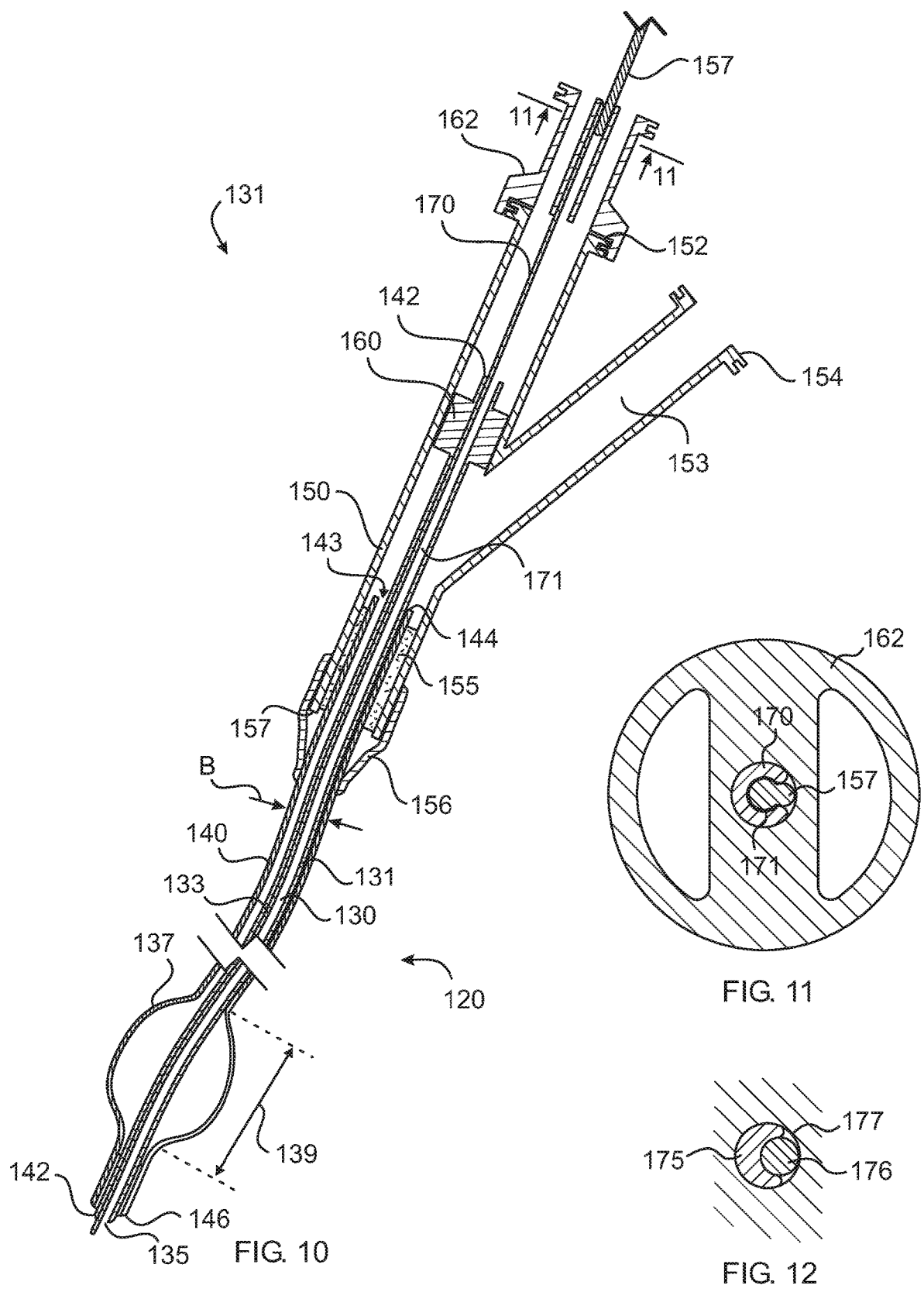

us 11,045,214 B2

INCREASED AXIAL LOAD CARRYING SHEATHED IRRIGATING BALLOON CATHETER

PRIOR APPLICATION

This is a continuation of U.S. patent application Ser. No. 14/606,922, filed 2015-Jan.-27 which is a continuation-in-part of U.S. patent application Ser. No. 14/520,052, filed 2014-Oct.-21 incorporated herein by reference.

FIELD OF THE INVENTION

The present invention relates to devices used for normalizing the flow of fluid in the narrow complexly-shaped body cavities including the lacrimal drainage system and the paranasal sinus system. More specifically, the invention relates to probes, catheters, stents and drainage tubes used in treating canalicular and nasolacrimal duct or nasal sinus obstruction caused by stenosis, lacerations or other trauma.

BACKGROUND

Rigid balloon catheters have been used to treat nasolacrimal and paranasal sinus obstructions as disclosed in my U.S. Pat. Nos. 7,169,163 and 8,317,816 respectively. Physical obstruction problems occurring in the lacrimal drainage system can be treated using a dual conduit irrigating and suctioning lacrimal catheter, having a dilatation balloon as disclosed in my U.S. Patent Application Publication No. 20090204142, incorporated herein by reference. Such catheters can be used to perform balloon catheter dacryocystoplasty (DCP) and dacryocystorhinostomy (DCR) both translacrimally and transnasally.

The above dual conduit catheter can be formed by a semirigid stainless steel hypotube coaxially penetrating through the sidewall and into the central lumen of a diametrically slightly oversized flexible plastic tube having a reduced thickness distal portion which can inflate as a dilatation or anchoring balloon. The hypotube can be connected at its proximal end to an irrigation or suction supply while the proximal end of the flexible tube can be connected to a compressed fluid balloon inflation supply.

As shown in Gould et al., U.S. Pat. No. 4,572,186, a V-shaped adapter assembly, also known as a hub, can secure the proximal ends of two catheter conduits in a single, hand-graspable structure.

Because a dual conduit catheter can be subjected to relatively large axial forces during insertion through or around obstructions or other barrier structures, unwanted slippage can occur between the various structures such as between a hypotube and portions of the flexible tube and/or hub, thus breaking the catheter and/or making it difficult for the surgeon to properly manipulate and place the catheter in the body. It has been found that axial forces of 10 Newtons run the risk of breaking the above catheter designs.

The instant invention results from attempts to avoid some or all of the above disadvantages.

SUMMARY

The principal and secondary objects of the invention are to provide for more efficient, simpler and safer procedures in the treatment of nasolacrimal obstructions and/or paranasal sinus obstructions. These and other objects are achieved by a sheathed tubular elongated semi-rigid balloon catheter tool including a bonding collar securing the probe portion to a hub.

In some embodiments, there is provided a device for the treatment of an obstruction in a patient's lacrimal drainage system which comprises: an oblong probe portion shaped and dimensioned to axially penetrate the lacrimal system of a patient; wherein said probe portion further comprises: an elongated substantially cylindrical body having a first outer diameter and terminating at a distal extremity and an opposite proximal extremity; said body being made from a hard, semirigid first material; a collar bonded to a portion of said body near said proximal extremity; said collar being made from a hard, semirigid second material; said collar having an outer peripheral surface having a second diameter greater than said first outer diameter; and, a hand graspable hub comprising a second rigid material different from said first material, said hub being secured to said outer peripheral surface along a hub/collar interfacing bond.

In some embodiments said hub/collar interfacing bond comprises an interface layer contacting said collar and said hub.

In some embodiments said interfacing bond further comprises a proximal bead axially bearing against said collar.

In some embodiments said hub/collar interfacing bond is capable of withstanding an axial sheer load in excess of 10 Newtons.

In some embodiments said outer peripheral surface comprises a surface area increasing structure.

In some embodiments said surface area increasing structure comprises a bearing surface having an axial component.

In some embodiments said outer peripheral surface of said collar is shaped to have a plurality of radial irregularities.

In some embodiments said radial irregularities comprise a plurality of axially spaced apart grooves.

In some embodiments said second diameter is at least twice as large as said first diameter.

In some embodiments said collar has a volume of at least ten times the volume of tube material within an axial zone of contact between said body and said collar.

In some embodiments said hub/collar interface comprises an amount of secondarily injected material contacting said hub and said collar.

In some embodiments said device further comprises: a flexible sheath coaxially engaged by said body; wherein said sheath comprises: a proximal end portion secured to said hub; and, a distal end portion comprising a balloon structure.

In some embodiments said device further comprises said body having an axial lumen extending from a proximal opening to a distal port.

In some embodiments said hub comprises: a first connector leading to a first passageway in fluid communication with said distal port; a second connector leading to a second passageway in fluid communication with said balloon structure.

In some embodiments said device further comprises an irrigation device or a suction device connected to said first connector.

In some embodiments said device further comprises an inflating device connected to said second connector.

In some embodiments said sheath has an axial length shorter than an axial length of said body.

In some embodiments said sheath is shaped and dimensioned to provide a gap between an outer surface of said body and an inner surface of said sheath.

In some embodiments said gap is formed by a fluid supplied to said second connector a pressure sufficient to deform said sheath.

In some embodiments said sheath comprises an expandable material selected to allow a compressed fluid to pass through said gap and inflate said balloon structure.

In some embodiments said balloon structure comprises a segment of said sheath having a reduced wall thickness along said segment.

In some embodiments said body further comprises: said distal extremity being blunted; and, said body having a total length between approximately 4 and 50 centimeters and an outer diameter between 0.125 and 5.0 millimeters.

In some embodiments said first material is taken from a group consisting of: stainless steel, bronze, silver, aluminum, titanium, brass, and alloy thereof, Kevlar, Nitinol, polymide, Dacron, nylon, EPTFE, polycarbonate, and PVC.

In some embodiments said first material comprises plastic or metal.

In some embodiments said first material and said second material are the same.

In some embodiments said probe portion has a maximum cross-sectional dimension of between about 1.0 millimeter and 4.0 millimeters.

In some embodiments said device further comprises an elongated reinforcing rod shaped and dimensioned to be inserted into said lumen.

In some embodiments said reinforcing rod is further shaped to have a semicircular cross-section, thereby forming an axial groove extending an entire length of said rod; said groove being sized to accommodate passage of a fiberoptic cable therethrough.

In some embodiments there is provided a method for manufacturing a balloon catheterization tool, said method comprises: separately forming a plastic hub; and a metal collared, elongated semi-rigid tubular body covered by flexible sheath; inserting the collared probe body into a passageway of the hub; injecting a liquid bonding material through an aperture in the hub surrounding the collar in enough quantity to contact both said hub and said collar; and, allowing said bond material to solidify.

In some embodiments there is provided a method for probing the integrity of a patient's canaliculus and nasolacrimal duct which comprises the steps of: inserting the device of claim 1 through the patient's punctum and canaliculus down the lacrimal sac; tilting the device angularly into alignment with the nasolacrimal duct; and, pushing the device through the nasolacrimal duct down to the nasal cavity; wherein said pushing comprises applying an axial force in excess of 10 Newtons to said hub.

In some embodiments said method further comprises engaging a stiffening rod diametrically sized to engage said lumen and having a length greater than said total length into said lumen prior to said step of inserting.

In some embodiments said method further comprises engaging a stiffening rod diametrically sized to engage said lumen and having a length shorter than said total length into said lumen prior to said step of inserting.

In some embodiments said method further comprises injecting an irrigation or tracer fluid through said device while said device is engaged in said patient's lacrimal system.

In some embodiments said method further comprises suctioning material through said device while said device is engaged in said patient's lacrimal system.

In some embodiments there is provided that in a semirigid balloon catheter tool including an oblong semirigid hollow tube having an axial lumen extending between a proximal opening and a distal port; an improvement which comprises: a reinforcing rod shaped to penetrate said lumen; said rod having a semicircular cross-section, thereby forming an axial groove extending an entire length of said rod; said groove being sized to accommodate passage of a fiberoptic cable therethrough.

In some embodiments there is provided a method for transnasally dilating a small, tight opening through human tissue into the nasal cavity which comprises the steps of: inserting transnasally the device of claim 27 toward a small, tight opening through human tissue into the nasal cavity; pushing the device through said opening until said balloon structure engages said opening; wherein said pushing comprises applying an axial force in excess of 10 Newtons to said hub; and, inflating said balloon structure.

In some embodiments said opening consists of an ostium or surgically prepared opening in the sphenoid sinus.

In some embodiments said opening consists of an ostium or surgically prepared opening in the maxillary sinus.

In some embodiments said opening consists of an ostium or surgically prepared opening in the frontal sinus.

In some embodiments said method further comprises plastically deforming said device prior to said inserting.

In some embodiments said plastically deforming is conducted according to a shape derived from a shaping rod previously inserted transnasally into said opening.

In some embodiments said plastically deforming comprises bending said probe portion to an angle of between about −90 and +160 degrees.

In some embodiments said method further comprises engaging a fiberoptic cable through an axial groove in said reinforcing rod.

In some embodiments said method further comprises injecting an irrigation or tracer fluid through said device while said device is engaged in said opening.

In some embodiments said method further comprises suctioning material through said device while said device is engaged in said opening.

In some embodiments there is provided a device for transnasally dilating a small, tight opening through human tissue into the nasal cavity, said device comprising: a tubular body having a proximal extremity, a proximal segment, a distal extremity, and a distal segment and a central lumen; a reinforcing rod element shaped to penetrate said lumen; a flexible sheath coaxially engaged by said body; an inflatable member formed on said sheath proximate to said distal segment; said inflatable member being capable of dilating said opening; wherein said tubular body lacks sufficient stiffness and column strength in absence of said reinforcing rod element inserted through said central lumen, to enable said inflatable member, when said inflatable member is deflated, to be inserted transnasally through the naris and into a nasal cavity and subsequently pushed through forces applied on said proximal segment into said opening; and wherein said tubular body has sufficient stiffness and column strength while said reinforcing rod element is inserted through said central lumen, to enable said inflatable member, when said inflatable member is deflated, to be inserted transnasally through the naris and into a nasal cavity and subsequently pushed through forces applied on said proximal segment into said opening; and, wherein said distal end is separated from said proximal end a distance sufficient to allow said proximal end to remain outside the nasal cavity while said inflatable member is being pushed into said opening.

The text of the original claims below is incorporated herein by reference as describing features in some embodiments.

BRIEF DESCRIPTION OF THE DRAWINGS

FIG. 10 is a diagrammatic cross-sectional side view, including partial enlarged views, of an irrigating/suctioning sheathed tubular balloon catheter including a hub bonding collar according to an alternate exemplary embodiment of the invention.

FIG. 11 is a diagrammatic cross-sectional end view the reinforcing rod, its connector and an inserted LED light source cable taken along line 11-11 of FIG. 10.

FIG. 12 is a diagrammatic cross-sectional end view of an alternate embodiment of an alternate reinforcing rod having a rounded crescent-shaped cross-section, its connector and an inserted LED light source cable having a circular cross-section.

DESCRIPTION OF THE EXEMPLARY EMBODIMENTS

The present exemplary embodiment will be described as it relates to treating a lacrimal obstruction. Modifications described further below can adapt the disclosed tool to treating some paranasal sinus obstructions.

Figure 1:
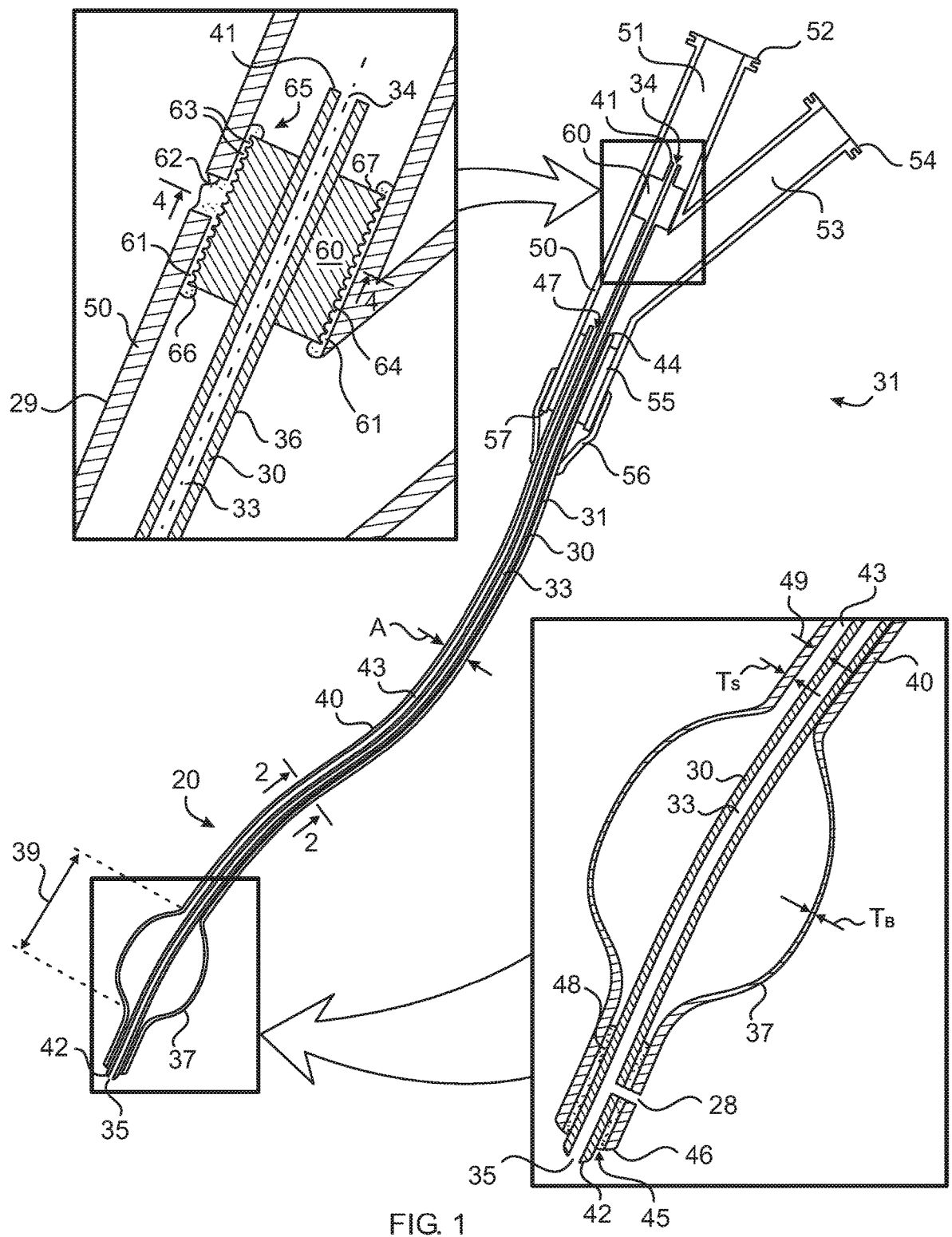
FIG. 1 is a diagrammatic cross-sectional side view, including partial enlarged views, of an irrigating/suctioning sheathed tubular balloon catheter including a hub bonding collar according to an exemplary embodiment of the invention.
Figure 2:
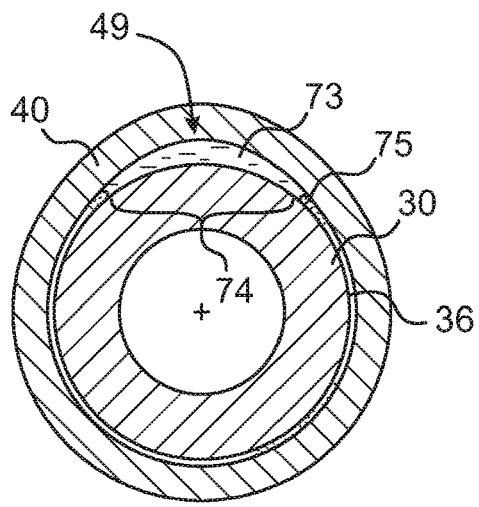
FIG. 2 is a diagrammatic cross-sectional end view the tube and sleeve taken along line 2-2 of FIG. 1.

Referring now to the drawing, there is shown in FIGS. 1 and 2, a multi-functional surgical tool 31 for the treatment of nasolacrimal obstructions. The tool includes an elongated, hollow, semi-rigid probe portion 20 having a distal, inflatable balloon 37. The probe portion connects at a proximal end to a rigid hub 50 which can be readily grasped by the hand of the surgeon to manipulate the tool. The hub also includes one or more openings for connecting supplies of pressurized fluid or suction.

The probe portion 20 is shaped and dimensioned for insertion through a patient's punctum and canaliculus, into the lacrimal sac and potentially through the lacrimal sac into the nasolacrimal duct, or through the medial wall of the lacrimal sac into the nasal cavity. The total cross-sectional diameter A of the uninflated probe portion can therefore have a maximum dimension of between about 0.25 and 10 millimeters, and typically about 1.0 millimeter for the present embodiment.

The probe portion 20 has enough rigidity to be maneuvered through the soft tissue twists and turns of the nasolacrimal network, but is flexible enough to bend around the small curves of the network without significantly cutting into those tissues. Once the distal end of the probe portion has passed through the obstruction, the balloon 37 can be inflated in vivo to dilate the tissue near the obstruction. Therefore, the probe must have a rigidity/flexibility and column strength sufficient to be pushed axially through the obstruction. Thus the probe portion can have a stiffness and a column strength capable of withstanding axial forces without buckling in excess of 10 Newtons and up to 15 Newtons for smaller cross-section devices and up to 200 Newtons for larger cross-section devices. It should be understood that the mechanical characteristics of the sheath do not appreciably contribute to the mechanical properties of flexibility and column strength of the sheathed probe tool. Thus it is primarily the mechanical characteristics of the semi-rigid tube that determine the flexibility and column strength of the tool.

Because it is to be introduced into the body, the probe portion 20 can be made of biocompatible materials.

The probe portion of the tool 20 includes an oblong, semi-rigid, tubular body or tube 30 coaxially engaging and secured within the central axial channel 43 of an oblong, flexible, tubular sheath 40. The balloon 37 can be formed on a distal portion 39 of the sheath. A gap 49 between the inner surface of the sheath and the outer surface of the semi-rigid tube can carry a pressurized fluid such as air to expand the balloon.

The tube 30 is shaped and dimensioned to have a substantially cylindrical outer surface 36. The tube 30 can be in the form of a conduit, such as a stainless steel hypotube, having an axial lumen 33 terminating at a proximal extremity 41 forming a proximal opening 34, and terminating at an opposite distal extremity 42 forming a distal axial port 35. Fluids can be injected, or suctioned through the axial lumen 33 of the tube. The distal extremity can be blunted to help avoid tissue abrasion during insertion. Optionally, one or more radial ports 28 can be formed through the sidewall of the probe, and if necessary through the sheath, and located a proximal distance from the axial distal port 35. The radial ports can provide a fluid passageway should the axial distal port be blocked.

The tube 30 can be made from material such as many stainless steels and other metals and alloys thereof such as titanium, silver, aluminum, bronze, brass, and synthetics like Kevlar, Nitinol, polymide, Dacron, nylon, EPTFE, polycarbonate or PVC may also be suitable. For many applications the probe can have an outer diameter $OD_t$ of between about 0.5 millimeter (0.02 inch) and 2.5 millimeters (0.1 inch), but could fall between about 0.1 millimeter (0.004 inch) and 6.0 millimeters (0.24 inch) for more specialized purposes such as pushing the tool through the medial sac wall. The axial lumen 33 of the tube can have a diameter of between about 0.001 millimeter (0.00004 inch) and 5.0 millimeters (0.2 inch).

The tube 30 can coaxially secure along a part of its outer surface 36 to the inner sidewall of the sheath 40. The sheath can have a proximal opening 47 at a proximal end 44 and a distal opening 45 at a distal end 46 which can be sealed to the probe by an annular layer of adhesive 48. The tube can thus pass through both the proximal opening 47 of the sheath and the distal opening 45 of the sheath. The radial ports 28 can be surrounded by adhesive 48 avoiding fluid communication between the lumen 33 of the tube and the axial channel 43 of the sheath.

The flexible sheath 40 includes a central axial channel 43 which can be dimensioned to be slightly diametrically oversized with respect to the tube so that there remains a gap 49 between the inner wall of the sheath and the outer wall of the tube so that a fluid 73 injected into the sleeve can readily flow through the gap to fill the balloon. The gap can annularly surround the tube in which case a layer of adhesive 75 can be used to secure portions of the sheath to the tube. The adhesive can be located at the distal end 46 and optionally near the proximal end 44. Alternately, as shown in FIG. 2, the gap can be formed along an angular zone 74 where there is an absence of the adhesive between the sheath and tube.

Figure 3:
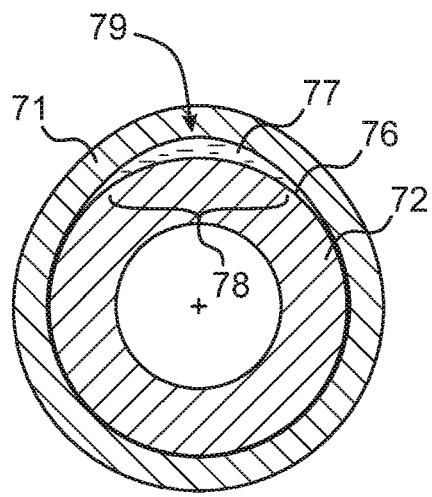
FIG. 3 is a diagrammatic cross-sectional end view the tube and sleeve taken along the probe portion showing a friction fitted sleeve.

Alternately, as shown in FIG. 3, the sheath 71 can be sized commensurately with the outer surface 76 of the tube 72 so that the interfacing surfaces of the tube and sheath intimately contact one another. The sheath can be retained on the tube by selecting the outer diameter of the tube to be larger than the unstressed inner diameter of the sheath thereby causing a friction fit between them, keeping the sheath lodged and in a stabilized position relative to the tube. This helps secure the entire length of the sheath to the tube and provides a smooth outer surface to the tool, enhancing its ability to be readily pushed into place in the lacrimal drainage system. In this embodiment the radially expanded gap 79 can be formed emobically under the influence of a pressurizing fluid 77. Thus the gap need not be annular, nor radially uniform but rather can be formed by a radial expansion of the resilient sheath material, and can occur at any angular location depending on the subtle weaknesses in the sheath material. Of course, in this embodiment the sheath must be made from a deformable material so that it can expand slightly under the force of the pressurized fluid.

The sheath can be made from a flexible, biocompatible synthetic material such as nylon. It can also be made of polyethylene terephthalate (PET), silicone, latex, polyurethane, polyvinyl chloride, cross-linked polyethylene, polyolefins, HPTFE, HPE, HDPE, LDPE, EPTFE, and block polymers, and/or other biocompatible elastomeric materials and combinations thereof. For most applications where nylon is the selected sheath material, the thickness of the sheath can be between about 0.001 millimeter (0.00004 inch) and about 5.0 millimeters (0.2 inch), and for most lacrimal obstruction treatment applications be about 0.15 millimeters (0.006 inch)

Referring back to FIGS. 1-2, the balloon portion 37 can made of the same material as the rest of the sheath 40 so long as it is resiliently expandable. The balloon portion can have a reduced thickness from that of the rest of the sheath, thus allowing it to expand relative to the rest of the sheath when under the influence of an internal pressurizing fluid. Thus, the sheath 40 can have a first given thickness $T_S$ in the non-balloon portion and a second, reduced thickness $T_B$ along a distal portion 39 to form an expandable balloon 37. Thus, the thickness of the balloon can be between about 0.05 millimeter (0.002 inch) and 10 millimeters (0.4 inch), and for most lacrimal obstruction treatment applications be about 0.10 millimeter (0.004 inch). The inflatable balloon can have an axial length 39 of between about 0.5 centimeter (0.2 inch) and 5 centimeters (2.0 inches), and for the present embodiment typically about 1.5 centimeters (0.6 inch). The balloon can be inflated using air pressures of between about 1.0 pound per square inch (psi) (0.7 atmosphere) and 30 psi (2.0 atmospheres) resulting in an inflated cross-sectional diameter of between about 1.0 millimeter (0.04 inch) and 20 millimeters (0.8 inch), and for most lacrimal obstruction treatment applications between about 2.0 millimeters (0.08 inch) and 6.0 millimeters (0.25 inch). It has been found that such fluid pressures can also adequately cause formation of an acceptable embolic gap between the tube and sheath leading from the hub to the balloon necessary in the embodiment of FIG. 3.

Alternatively, a balloon segment made of a more easily expanded material can be attached to the distal end of the sleeve.

Referring now primarily to FIG. 1, the rigid hub 50 can be secured over the proximal extremity 41 of the tube 30 and the proximal end 44 of the sheath 40. The hub includes a first passageway 51 leading from a first luer-lock or other type of connector 52 to the proximal opening 34 to the tube 30, and a second passageway 53 leading from a second luer-lock or other type of connector 54 to the proximal opening 47 to the sheath 40. The two passageways 52,54 are sealed from one another; and thus there is no fluid communication path therebetween.

The sheath 40 can be secured to the hub 50 by a hollow cylindrical rigid plastic spacer 55 bonded by layers of adhesive (not shown in the drawing) or other means known in the art. A flexible vinyl boot 56 seals the distal edge 57 of the hub to the outer surface of the sheath extending distally therefrom.

The hub 50 can be made from a durable, rigid, injection moldable material such as polycarbonate, or other plastics and stainless steel or other metals. When this material is different from the material of the semi-rigid tube, it can have a higher coefficient of thermal expansion and a lower thermal conductivity than the material of the tube. This mismatch in material properties can lead to weakness along a mechanical bond between the tube and hub.

The total insertable length of the tool measured from the distal extent of the boot 56 to the distal extremity 42 of the tube 30 may be within range from between about 1 centimeter (0.4 inch) and 50 centimeters (20 inches), and is typically about 15 centimeters (6 inches) for the present embodiment.

Figure 4:
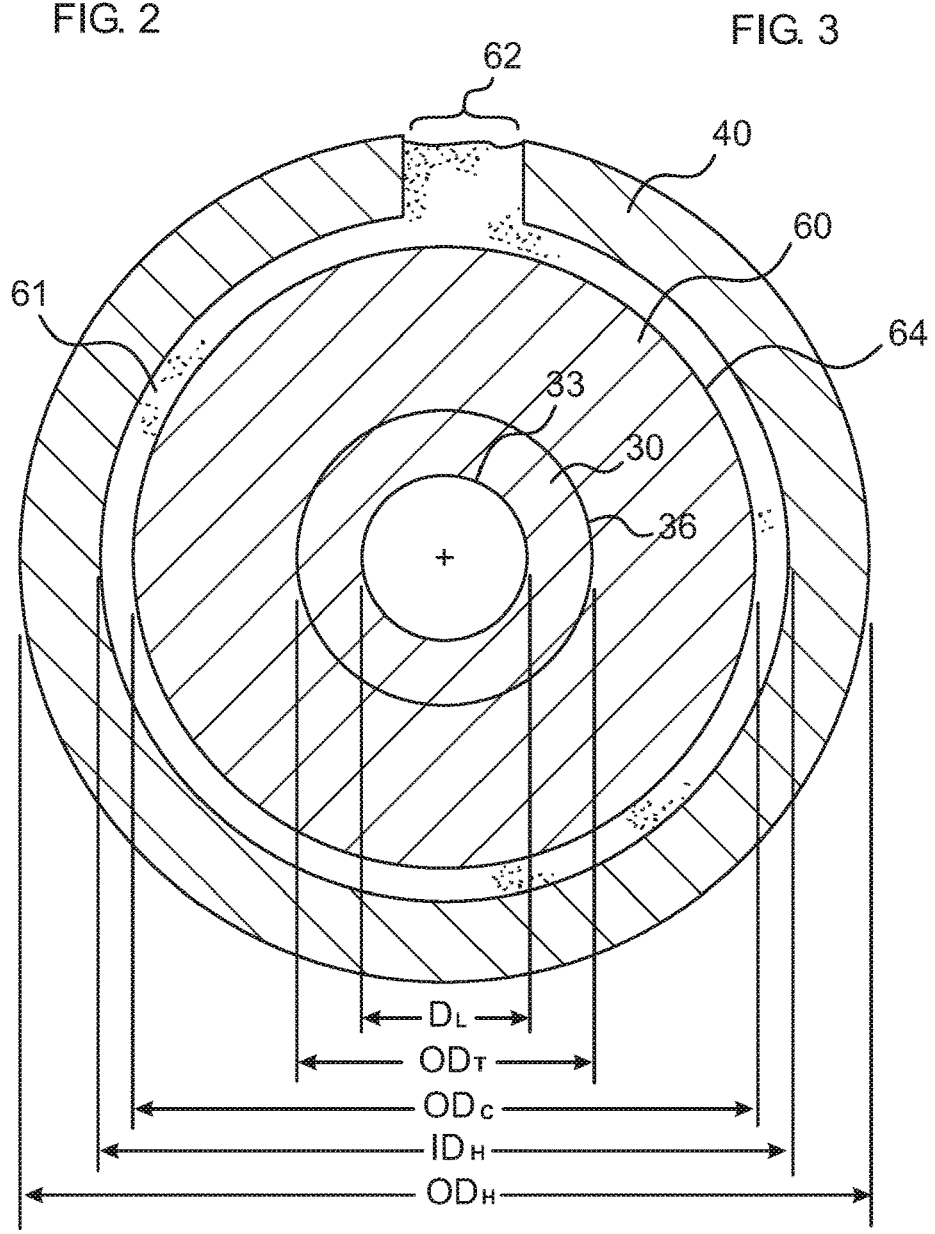
FIG. 4 is a diagrammatic cross-sectional end view a combination of the collared tube and hub taken along line 4-4 of FIG. 1.
Figure 5:
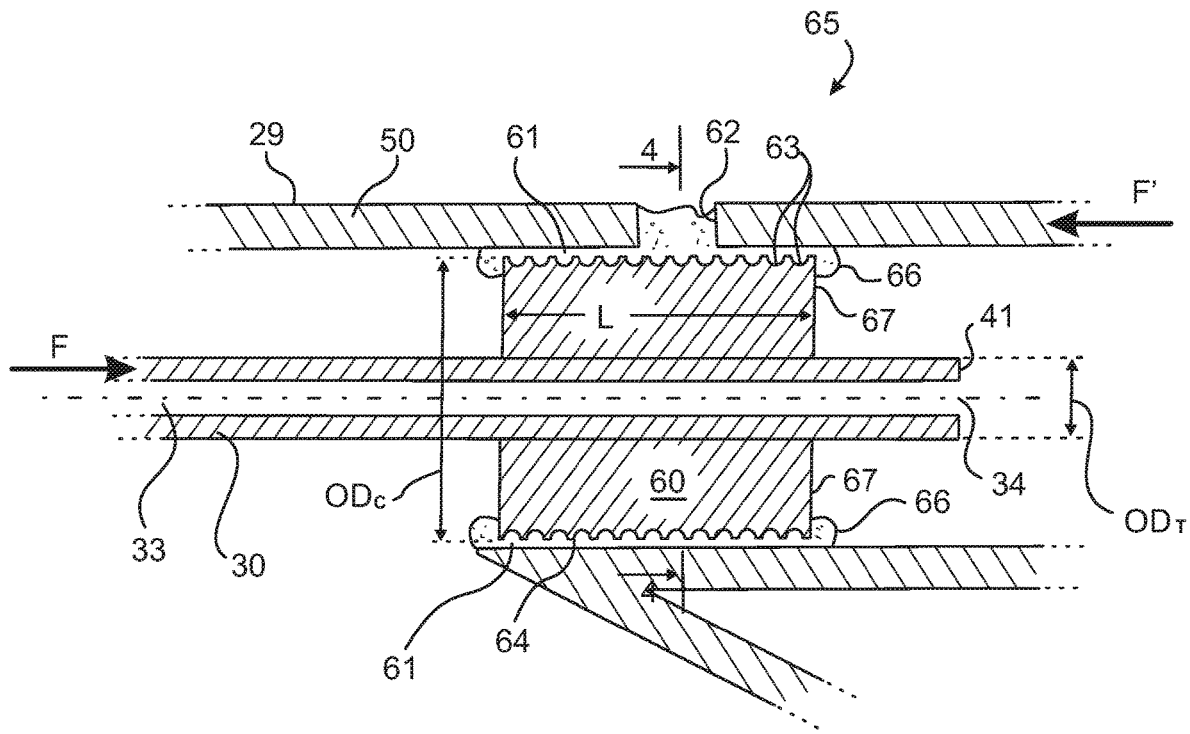
FIG. 5 is a diagrammatic cross-sectional enlarged side view showing the sheer forces on the hub bonded collar.

Referring to FIGS. 1, 4 and 5, the tube 30 can be secured to the hub 50 through a rigid collar structure 60 welded to the cylindrical outer surface of the tube near its proximal extremity 41. The peripheral outer surface 64 of the collar is bonded to a corresponding inner surface of the hub's first passageway 51 along a hub/collar bond 65 for the tube by an adhering layer of adhesive 61 injected during assembly of the tool through an aperture 62 in the sidewall of the hub over the location of the collar. The adhering layer can be a secondarily injected amount of the same material that forms the hub. For example, the hub can be formed from a first injection molded amount of polycarbonate plastic, and the adhering layer can be formed from a subsequent, secondarily injected amount of adhesive such as epoxy or molten plastic.

The bond 65 between the collar and the hub effectively seals the first passageway 51 of the hub over the proximal opening 34 to the tube 30. Optionally, the injection of an overabundance of bond material creates a proximal bead 66 of bond material bearing against a proximal facing edge of the collar to further secure the collar and tube from being dislodged by higher magnitude axial forces on the tube. In other words, the proximal bead of bond material 66 forms an axial barrier against which a collar bearing surface 67 bears. This axial barrier thus has an axial component against which the collar bears, thereby allowing the tube to withstand larger axial mechanical load without breaking free from its axial position within the hub.

The collar has an outer diameter $OD_c$ which is at least twice as large as the outer diameter of the tube $OD_T$ and can be close to the inner diameter of the hub passageway $ID_H$. In this way the surface area forming the bond between the collar and the hub is increased and thus strengthened. Because the outer diameter of the collar is selected to be close to the inner diameter of the hub passageway, the secondary injection of adhesive or hub material between these two surfaces is done in a controlled, localized manner allowing minor controlled adjustment to the secondary injection pressure to adjust the size of the resultant proximal bead 66.

The outer surface of the collar can be shaped to have a number of axially spaced apart circumferential grooves 63, or otherwise roughened through scoring or grit blasting for example, in order to form radial irregularities to further increase the available surface area and to form bearing surfaces which resist axial sheer forces, and thus forming a more rugged bond between the collar and the hub. These axial bearing surfaces also form an axial barrier against which corresponding surfaces of the bond material bears.

It has been found that the collar-to-hub bond can, as a minimum for most common nasolacrimal catheters, withstand an axial load F in excess of 130 Newtons. This load is applied as a sheer force of the bond due to the countering reactive force F'. In practice it has been found that the bond can often withstand a load in excess of 175 Newtons.

The coefficient of thermal expansion ("CTE") or simply the thermal expansion of a material is defined as the ratio of the change in length per degree Centigrade to the length at 25 degrees C. It is usually given as an average value over a range of temperatures. The CTE of stainless steel is between about 10 ppm/degree C. and 17 ppm/degree C., whereas polycarbonate is typically between about 65 ppm/degree C. and 70 ppm/degree C. Therefore, polycarbonate expands far more than stainless steel under the influence of heat.

The thermal conductivity ("TC") of a material its property to conduct heat, and is measured in watts per meter kelvin. The TC of stainless steel is between about 16.3 W/(m•K) and 24 W/(m•K), whereas polycarbonate is typically between about 0.19 W/(m•K) and 0.22 W/(m•K). Therefore, stainless steel is a far better thermal conductor than polycarbonate.

Although the increase in area of contact between the collar and hub could be expected to improve the bond between them, the increase in size of the zone of contact will undergo larger stresses due to thermal displacement. In other words, as the bond interface grows in diameter the bond will be subject to greater mechanical stress due to the thermal expansion mismatch between the hub and collar, thus weakening the bond. Thus, merely increasing the surface area of the bond can be counter intuitive.

The warmth of the surrounding body tissues and the temperature of fluids coursing through the catheter can also lead to thermal expansion mismatch stresses. For example, the warmth of the surgeon's fingers and surgical lights on the hub may warm it more than the tube or collar, especially when colder fluids are injected. Further, the presence of the collar reduces the amount of hub material surrounding the bonded zone of contact between the plastic and metal. Having less relatively insulating hub material, having a relatively low coefficient of thermal conductivity, means the bond zone is warmed more quickly than it would have been without the collar. This occurs during a time when the hub is being grasped hard by the surgeon while it is being pushed through the obstruction and thus subjected to its greatest axial load.

However, unexpectedly, it is believed that the increased heat sink capacity of the collar helps reduce the expansion mismatch at least temporarily because of the greater volume of material present. So, even though outer portions of the hub is being warmed, inner portions in close contact with the collar are kept cooler. In addition, because of the higher TC of the tube relative to the hub, thermal energy is rapidly transported to the collar, expanding it before the hub material surrounding the collar is heated.

Therefore, increasing the volume of material in the collar can increase the heat sink effect. It has been found that the volume of material in the collar can be least five times the volume of tube material within an axial zone of contact between said tube and said collar. This zone of contact can correspond to the axial length L of the collar. For cylindrical tube and collar shapes, the volume of collar material $V_c$ can be expressed thus:

$$V_c = L * \Pi[(OD_c/2)^2 - (OD_t/2)^2]$$

And the volume of tube material $V_t$ within an axial zone of contact can be express thus:

$$V_t = L * \Pi[(OD_t/2)^2 - (D_L/2)^2]$$

For the present embodiment where the outer diameter of the tube $OD_t$ is between about 0.2 millimeter (0.008 inch) and 6.0 millimeters (0.24 inch), and for most lacrimal obstruction treatment applications about 0.5 millimeters (0.02 inch), the outer diameter of the collar $OD_c$ can be between about 0.5 millimeter (0.02 inch) and 20 millimeters (0.8 inch), and for most lacrimal obstruction treatment applications about 3.0 millimeters (0.12 inch). The axial length of the collar can be between about 0.1 millimeter (0.004 inch) and 25 millimeter (1 inch), and for most lacrimal obstruction treatment applications about 5 millimeters (0.2 inch). Those skilled in the art will readily appreciate the volume calculations for most other shapes.

Figure 6:
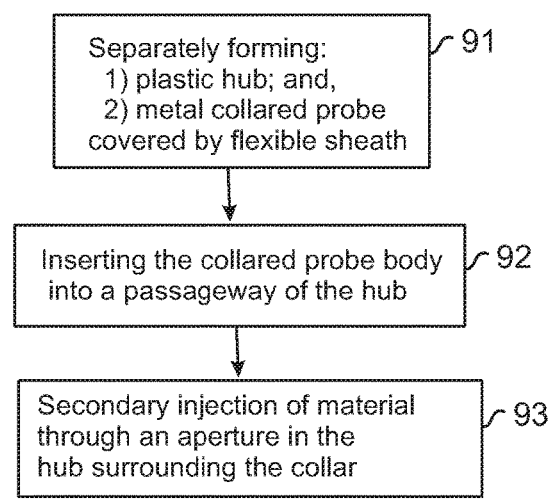
FIG. 6 is a diagrammatical flow chart of assembly steps to form the sheathed probe of FIG. 1.

Referring now to FIG. 6 there is shown the primary manufacturing step of secondary injection of hub material. The hub and the collared tube, covered by a flexible sheath, are formed separately 91. The hub can be formed by a primary injection molding process. The tube can be formed by means well-known in the art. The distal extremity of the tube can be burnished at this time to form a rounded tip. The collar can be welded to the tube near its proximal end. The tube can be inserted into the flexible sheath, and subjected to a heating process to shrink the sheath onto the tube to form the probe portion assembly. The probe portion assembly can be inserted into the passageway of the hub 92 and kept at a proper axial position with respect to the hub while a secondary injection molding process is conducted 93 to inject hardenable material into the passageway in intimate contact with both the collar and the inner surface of the hub passageway. The material can be an molten plastic material similar to the material of the hub, epoxy glue, or other hardenable martial bondable to the hub material and the collar material. The material is allowed to harden forming a bond between the collared tube and the hub.

The above-described surgical tool can be used in a variety of surgical interventions as explained below.

Figure 7:
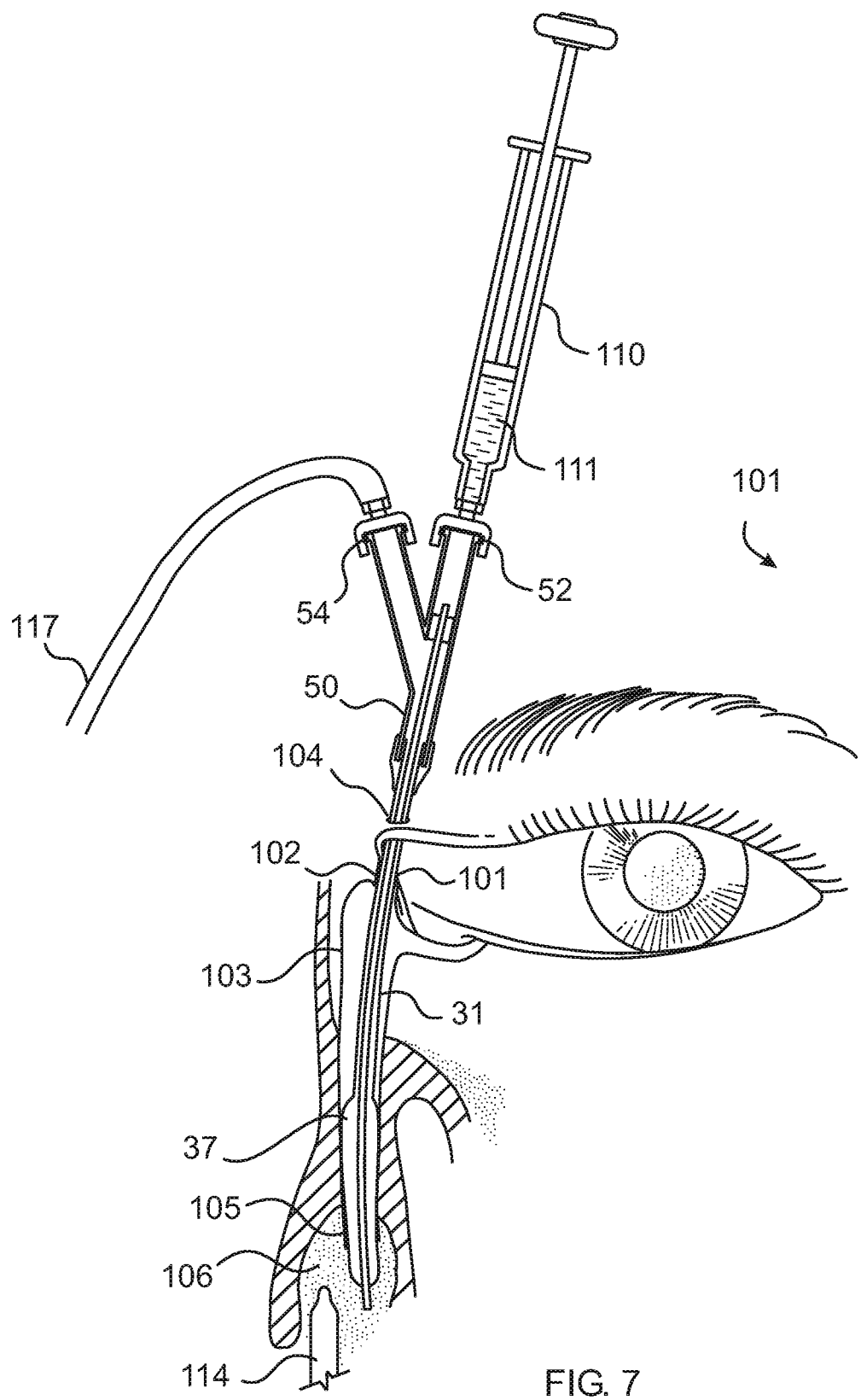
FIG. 7 is a diagrammatical illustration of the use of the tool in a DCP procedure.

Referring now to FIG. 7, in a balloon catheter DCP procedure, the surgeon begins dilating the punctum with a punctal dilator before inserting the sheathed semi-rigid tube probe portion of the tool 31 in a balloon deflated state through the punctum 101 and canaliculus 102 down to the lacrimal sac 103. The probe portion can first be inserted through a punctum 104 in the upper or lower eyelid to help properly orient the tool to the lacrimal sac. A barrier is felt when the probe encounters the medial lacrimal sac wall and lacrima fossa. The tool is then retracted about 0.5 millimeters and is tilted about 90 degrees into alignment with the nasolacrimal duct 105. The probe is then pushed down the nasolacrimal duct and into the nasal cavity 106.

A syringe 110 can be connected directly to the connector 52 on the hub 50 of the tool 31. Alternatively, the syringe can be connected via a flexible tube. The syringe can be loaded with fluorescein or methylene blue stained fluid 111 or any other tracing fluid. The fluid is injected to irrigate through the tube and into the nose. Traces of the fluid can be recovered in the nose with a suction device 114. A lack of fluid in the nose indicates that the tool has not penetrated all obstructions and reached the nose, or perhaps has taken a divergent passage through tissues surrounding the nasolacrimal duct. The surgeon can then either push with greater force or pull the tool slightly and drive it into the nasal cavity at a slightly different angle. Detection of the tracing fluid in the nose is a positive indication that all obstructions have been penetrated and the tool has followed a non-divergent path. It should be noted that the surgeon does not have to perform the difficult and sometime impossible task of touching the tip of the tool in the nose with another metal instrument in order to confirm that the tool has duly entered the nasal cavity.

While the tool remains emplaced, a pressurized fluid supply line 117 can be connected to the sheath connector 104 at the proximal end of the tool hub 50. An inflating fluid is sent down the sheath to inflate the balloon 37 and dilate the stenoic nasolacrimal duct 105. If necessary, the balloon can deflated and pulled more proximally before a new inflation cycle is performed. The procedure can be repeated as many times as it may be necessary to dilate the entire duct and the sac-duct junction. The balloon is deflated and withdrawn from the lacrimal system. A syringe having a cannula is inserted into the canaliculus, and irrigation with a tracer liquid can be made. If irrigation is not successful the tool may be pushed back before repeating the inflation procedure until tracer fluid recovery in the nose confirms that all obstructions have been corrected.

If significant bleeding occurs during the procedure, the syringe 110 can be removed and the connector 52 is connected to the suction device in order to remove the blood.

Although, it is the discretion of the surgeon to initially use a standard probe to verify the patency of the pathway from the punctum through to the nasal cavity, an advantage of using the sheathed semi-rigid tube tool is that this initial step can be avoided. The patency can be verified by the probe portion of the tool during its initial insertion. Further, the entire procedure can be performed using only a single insertion of the tool. This helps reduce irritation or other damage to the tissues involved.

Figure 8:
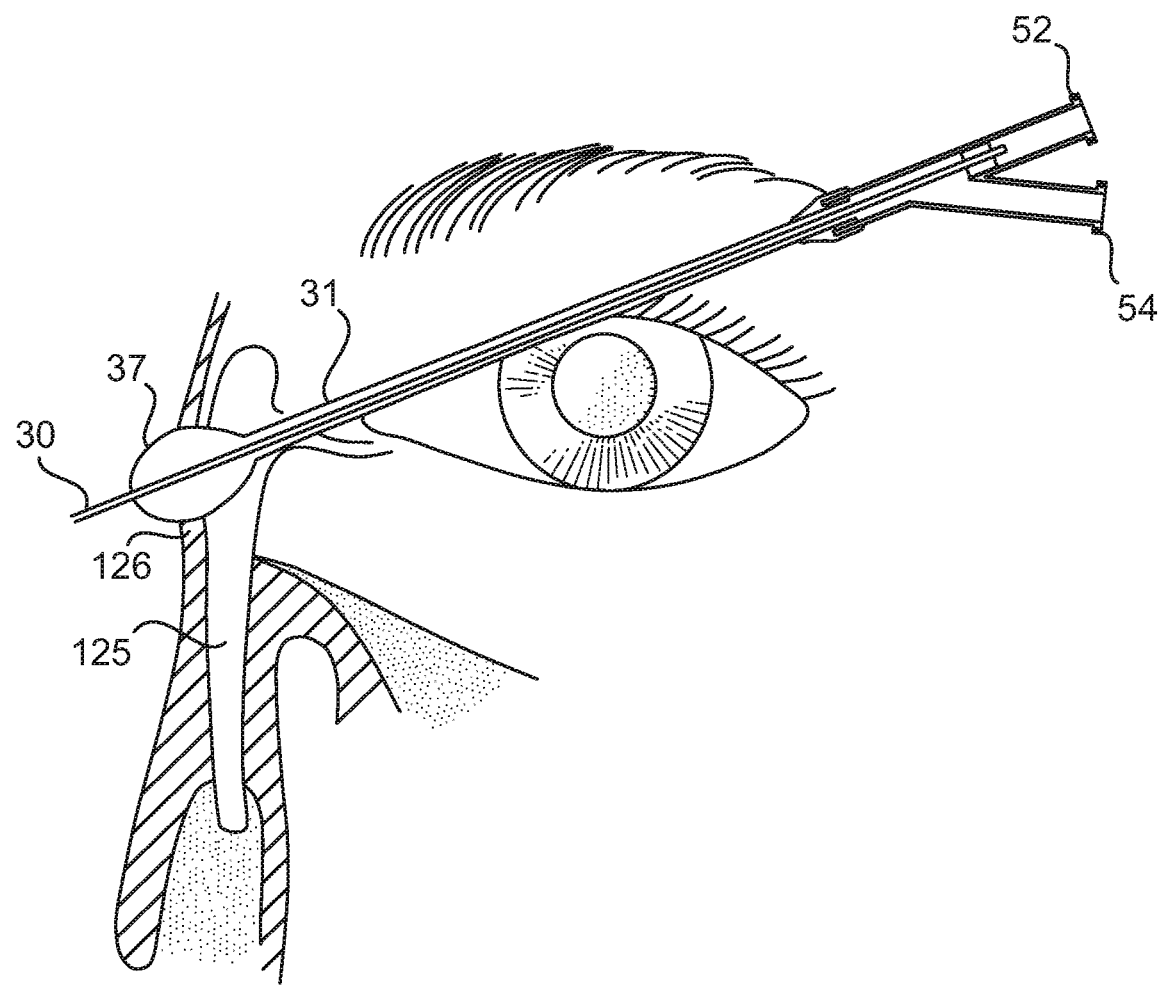
FIG. 8 is a diagrammatical illustration of the use of the tool in a translacrimal DCR procedure.

Referring now to FIG. 8, a balloon catheter DCR can be performed by inserting the probe portion of the tool 31 as described above in connection with a DCP into the lacrimal sac. Optionally, a standard probe may be pushed through one or more times to make sure there exists an opening. The probe portion of the tool is then pushed through the inferomedial wall of the sac, lacrimal fossa, and lateral nasal wall 126 into the nose. The distal end of the tool can be visualized endoscopically, or a syringe can be connected to the connector 52 to inject a tracer fluid through the probe 30 of the tool. The presence of tracer fluid in the nose confirms the distal end of the tool is in the nasal cavity. The tool can be further pushed through multiple adjacent areas to enlarge the opening and push bone chips of lacrimal fossa bone and possibly ethmoid bone into the nasal cavity. The irrigation/confirmation step can be repeated. The syringe can then be replaced by the suction device, and blood and tissue debris suctioned. Bleeding is usually more profuse than in a DCP and suctioning may have to be performed during the entire operation.

Inflation of the balloon 37 is accomplished by connecting the sheath connector 54 to an inflation device as described earlier. Balloon dilatation of the area about the opening into the inferomedial wall 126 completes the operation. The tool in then withdrawn.

Figure 9:
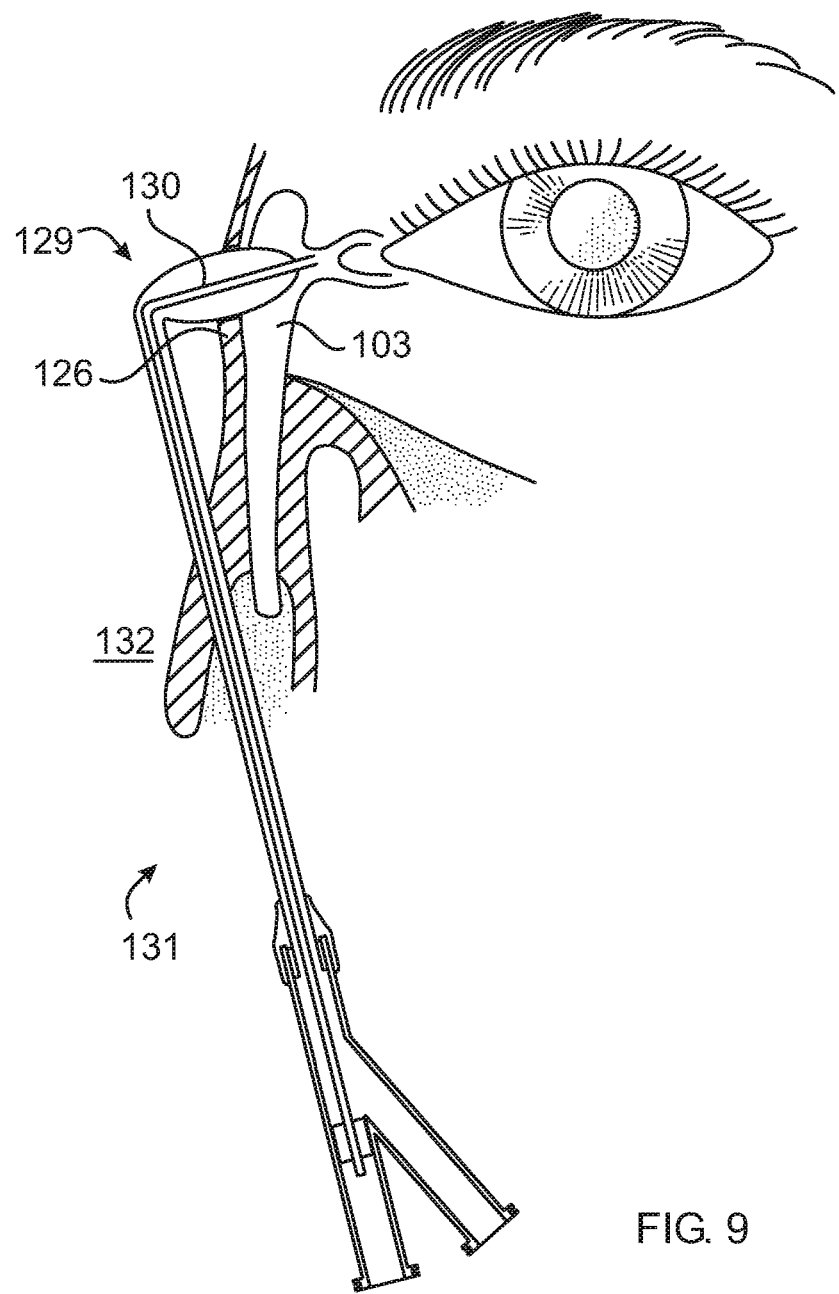
FIG. 9 is a diagrammatical illustration of the use of the tool in a transnasal DCR procedure.

As shown in FIG. 9, the performance of a transnasal balloon catheter DCR can be performed basically in the same manner as the above-described trans-lacrimal DCR, except that after probing and piercing of the inferomedial wall and lateral nasal wall, a modified transnasal embodiment tool 131 can be brought up through the external naris, up the nasal cavity 132 and pushed through the opening in the lateral nasal wall, lacrimal fossa, and inferomedial wall 126 and into the lacrimal sac 103.

The modified tool 131 has a distal segment 129 bent at an angle of between about 10 and 170 degrees, and is typically about 90 degrees. The transnasal embodiment tool has a generally larger diameter to make the tool stiffer in order to accommodate the larger lateral forces required to insert the bent portion through the opening.

A suction procedure can be performed through the probe 130, and then a dilatation procedure as described above. After disconnecting the suction device, irrigation may be performed.

The tubular probe 131 can also be used at that time to deliver medications into the nasolacrimal duct.

The entire tool 131 including its sheath can be removed, whereupon the surgeon can insert a short cannula of about 1.0 centimeter in length into the punctum and canaliculus. With syringe, a tracer fluid can then be injected through the cannula into the nasolacrimal network. If none of the fluid is recovered in the nose, the procedure must be repeated.

In lieu of a tracer fluid, a radio-opaque or isotopic solution can be injected. An x-ray or radiation detecting machine can then be used to confirm the proper penetration of the tool.

It can thus be understood that the flexibly sheathed semi-rigid tube probe of the invention is a very versatile instrument that can be used not only for probing the nasolacrimal ducts, but also to perform intubation, irrigation and even suction of obstructive material.

In this way a surgeon can confidently apply an axial force of greater than 100 Newtons to a balloon carrying sheathed irrigating semi-rigid probe in attempting to overcome blockages.

Nasal Sinus Embodiments

The sheathed tubular elongated semi-rigid balloon catheter tool can also be used in the treatment of obstructions in the paranasal sinuses.

Referring now to FIGS. 10 and 11, there is shown an alternate exemplary embodiment of a multi-functional surgical tool 131 for the treatment of paranasal sinus obstructions. The tool includes an elongated, hollow, semi-rigid probe portion 120 having a distal, inflatable balloon 137. The probe portion connects at a proximal end to a rigid hub 150 which can be readily grasped by the hand of the surgeon to manipulate the tool. The hub also includes one or more openings for connecting supplies of pressurized fluid or suction. A hollow stiffening rod 170 coaxially engages the lumen of the tube to adjust its mechanical properties.

The probe portion 120 is shaped and dimensioned for insertion through a patient's nasal cavity and to be pushed through a stenotic or otherwise obstructed paranasal sinus ostium or surgical opening. The total cross-sectional diameter B of the uninflated probe portion can therefore have a maximum dimension of between about 0.25 millimeter (0.01 inch) and 10 millimeters (0.4 inch), and typically about 2.0 millimeters (0.08 inch) for the present embodiment. Once the distal end of the probe portion has passed through the obstruction, the balloon 37 can be inflated in vivo to dilate the tissue near the obstruction.

In this embodiment the probe portion 120 need not have enough column strength or stiffness to be pushed through a stenotic or otherwise obstructed paranasal sinus ostium or surgical opening but rather can be receive a stiffening rod to achieve a stiffness and column strength appropriate for the particular region or condition being probed. Therefore, only with the reinforcing rod inserted can the probe portion can have a rigidity/flexibility and column strength sufficient to be pushed axially through the obstruction. Thus the probe portion with reinforcing rod inserted can have a stiffness and a column strength capable of withstanding axial forces without buckling in excess of 10 Newtons and up to 15 Newtons for smaller cross-section devices and up to 200 Newtons for larger cross-section devices. It should be understood that similarly to the nasolacrimal embodiments described above, the mechanical characteristics of the sheath do not appreciably contribute to the mechanical properties of flexibility and column strength of the sheathed probe tool including the reinforcing rod. Thus it is primarily the mechanical characteristics of the rod engaged tube that determine the flexibility and column strength of the tool.

Because it is to be introduced into the body, the probe portion 120 can be made of biocompatible materials.

In the following paranasal sinus embodiments the tube 130 of the balloon catheter can be made of a material that does not necessarily have the same flexibility requirements of the nasolacrimal embodiment described above. However, the probe portion can be made to have sufficient plastic deformability to maintain a shape e.g. a bend or curve that is placed upon it by the surgeon. The probe portion can be shaped or bent by the surgeon as needed during use in one or more of the paranasal sinuses.

Thus, the tube body 130 of the probe portion of a balloon catheter tool 131 for use in treating obstructions in one or more paranasal sinuses can have a greater flexibility. That flexibility can be adjusted by engaging a plastically deformable reinforcing rod 170 through the lumen 133 of the tube 130 of the balloon catheter tool. The reinforcing rod can have a luer lock connector 162 that can be attached/screwed into the luer lock 152 on the proximal hub 150 and provide an opening for engaging a fiberoptic cable 157.

The reinforcing rod 170 can extend to the distal extremity 142 of the tube 130 or may be longer and extend out the distal port 135, or be slightly shorter and terminate just inside the distal extremity of the tube. The reinforcing rod may be made of nitinol which is flexible but regains its original shape after the bending force or constraint is removed. It can thus be easily removed from the balloon catheter tube after the desired bend is placed in the tube. Other materials could keep their new bent shape and be difficult or impossible to remove from the tube. The reinforcing rod 170 can be made from stainless steel, annealed stainless steel or other metals, plastics or other synthetic biocompatible materials providing the necessary mechanical properties.

The reinforcing rod 170 may be removed after or temporarily during the placement of the balloon catheter in order to insert a fiberoptic cable 157 with a LED or other light. The light may be white, red or other color. The fiberoptic cable may have a luer lock connector (not shown) that can be screwed onto the luer lock on the hub or the lock on the reinforcing rod if present. The LED light will illuminate the sinus to help confirm to the surgeon that the catheter has entered the sinus.

As shown in FIG. 11, the reinforcing rod 170 can have semicircular in cross section such as a substantially C-shaped cross-section providing a central axial groove 171 extending the entire length of the reinforcing rod. The fiberoptic light cable 157 can be inserted at the same time with the reinforcing rod. This gives the surgeon the ability to illuminate the sinus throughout the insertion of the catheter into the sinus.

Alternately, as shown in FIG. 12, the reinforcing rod 175 can have semicircular in cross section such as a substantially crescent-shaped cross-section, and the fiberoptic cable 176 (which has a circular cross-sectional shape) can be partially inside and partially outside the crescent-shaped rod. The reinforcing rod and fiberoptic cable can thus be simultaneously carried within the lumen 177 having a substantially circular cross-sectional shape.

The tube 130 can be used to suction material e.g. blood or pus from the sinus. The tube can be used for irrigation of the sinuses or nasal cavity with water or saline, radio-opaque dye, other dyes such as fluorescein.

An important feature of the present embodiment is that the angular shape of the catheter probe portion 120 need not be preset. In other words, the probe portion can be straight or have any curve or shape when it is taken out of the package by the surgeon. However, the shape of the catheter can be changed by the surgeon as needed either through plastic deformation of the tube or the reinforcing rod, or both.

The present embodiment of the balloon 137 is about 6 millimeters (mm) in inflated diameter and 18 mm in length. However, it may be from 2 mm in diameter to 15 mm in diameter and be from 2 mm to 30 mm in length. A variety of sizes can be provided in kit form to give the surgeon choices.

The tube 130 may be made of stainless steel, annealed stainless steel, other metals, plastics, silicone or other synthetic materials, plastics, silicone or other synthetic materials with wire mesh or other reinforcing material within.

The length of the probe portion 120 of the catheter in the present embodiment is 6 inches (range 2 inches to 20 inches).

The outside diameter of the tube is 1.5 mm (range 0.5 to 5 mm) and wall thickness is 0.005 inch but may vary from 0.001 to 0.3 inch.

The balloon in the ideal embodiment is made of nylon but may be made of PET or any other biocompatible expandable material.

The above-described surgical tool can be used in a variety of surgical interventions involving the treatment of blockages occurring in the paranasal sinuses as explained below.

First proper preparation of the nasal cavity such as a septoplasty, ethmoidectomy, turbinectomy, turbinate infracture, creating a surgical opening or procedures if indicated are performed by the surgeon.

With respect to the Sphenoid sinus as shown in FIG. 12:

For the sphenoid sinus the probe portion 120 of the catheter tool is usually close to straight i.e. angle of 0 degrees but may be from −90 to +160 degrees.

The sphenoid sinus ostium may be approached and entered directly using first a shaping rod if needed. The shaping rod is bent or curved to the desired angle. It is placed into the sphenoid sinus ostium. The sphenoid sinus ostium is located inferior to the superior turbinate and between the middle turbinate and nasal septum. In some cases the posterior inferior portion of the middle turbinate must be resected to allow the shaping rod to gain the sphenoid sinus ostium. In some cases an ethmoidectomy must be performed first in order to gain access to the sphenoid sinus and its ostium.

The shaping rod is then removed. The balloon catheter with the stiffening or reinforcing rod in place is bent to the same shape as the shaping rod. In some cases the balloon catheter tube is bent to the desired curve or angle without using the shaping rod. The balloon catheter with the stiffening rod is then pushed into the sphenoid sinus. This is usually done with the reinforcing rod (or reinforcing rod and LED light and cable) inside the balloon catheter, but may be done on the balloon catheter alone and then the reinforcing rod or reinforcing rod and LED light and cable placed as a second step. The surgeon then inserts the balloon catheter with reinforcing rod (and LED or other light type in some embodiments) through the sphenoid sinus ostium or surgically prepared opening in the sphenoid sinus into the sphenoid sinus cavity. The location is confirmed by visualization of the LED or other light illuminating the sphenoid sinus. In some cases the surgeon may move or rotate the catheter to visualize the light movement inside the sinus. After confirming the proper placement of the balloon catheter the surgeon connects the inflation port 154 of the hub 150 to the inflation device. The balloon 137 is inflated to nine atmospheres (range 1 to 30 atmospheres) for the desired time of 60 seconds (range 1 second to 5 minutes). The balloon catheter is then deflated. A second inflation or more inflations can be performed if needed. The balloon catheter can be withdrawn to allow inspection of the ostium or surgical opening if desired. It can then be reinserted if needed for additional inflations. Further, the reinforcing rod can be removed and suction or irrigation performed through the tube 130 if needed.

Figure 13:
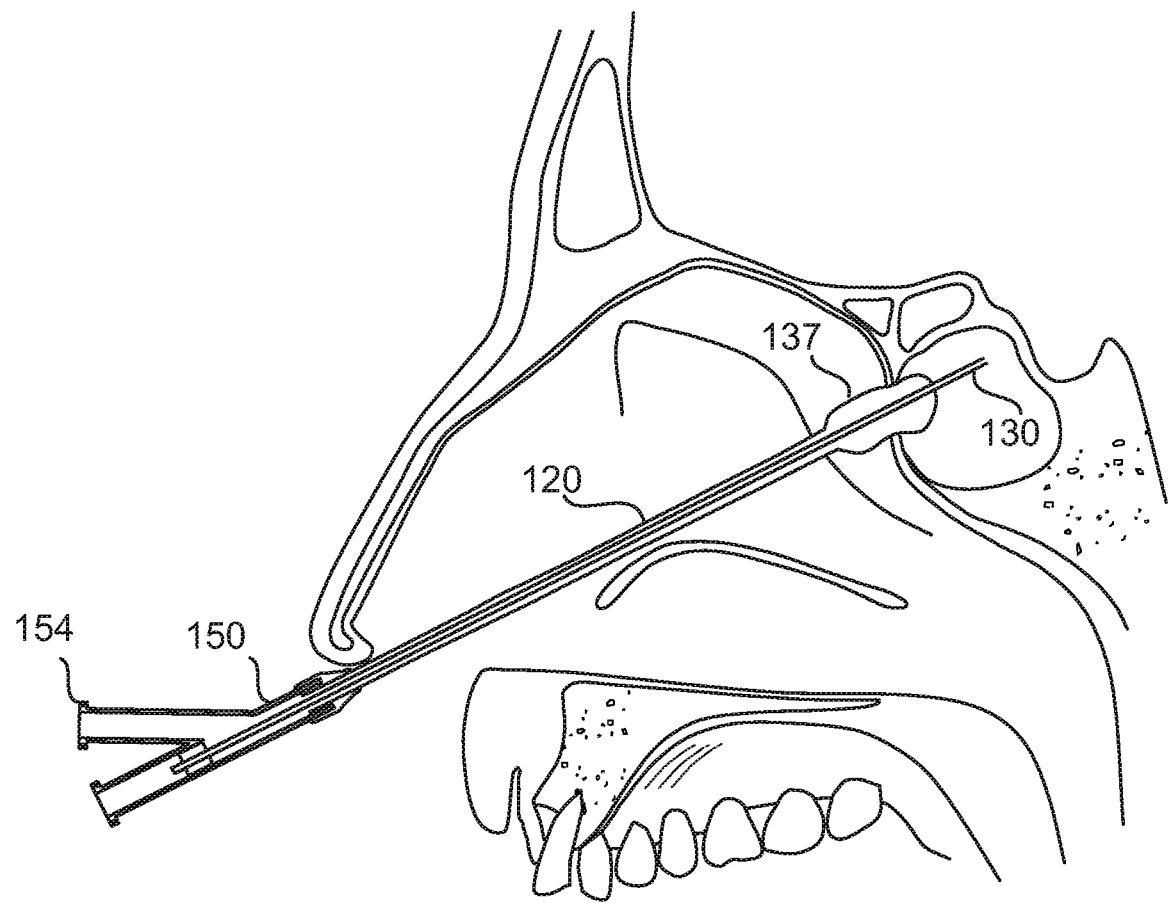
FIG. 13 is a diagrammatical illustration of the use of the tool in a sphenoid sinus opening dilatation procedure.

With respect to the Maxillary sinus as shown in FIG. 13:

A similar process is used for the maxillary ostium and maxillary sinus. The usual angle of the distal balloon section with respect to the more proximal section of the probe portion 120 is about 120 degrees but may from 50 to 200 degrees.

The middle meatus and maxillary sinus ostium are visualized endoscopically. A set of shaper rods is provided to the surgeon. Alternatively, the surgeon bends a shaper rod to a desired shape. The shaper rods are then placed in the middle meatus and gently into the maxillary ostium. If the angle is not optimal then a different shaper rod is obtained. This process is repeated until the ideal angle of shaper rod that easily goes into the maxillary sinus ostium is obtained. The sinus balloon catheter tube is then bent to the same shape as the ideal shaper rod. This is usually done with the reinforcing rod (or reinforcing rod and LED light and cable) inside the balloon catheter, but may be done on the balloon catheter alone and then the reinforcing rod or reinforcing rod and LED light and cable placed as a second step. The surgeon then inserts the balloon catheter with reinforcing rod (and LED or other light type in some embodiments) through the maxillary ostium or surgically prepared opening in the maxillary sinus into the maxillary sinus cavity. The location is confirmed by visualization of the LED or other light illuminating the maxillary sinus. In some cases the surgeon may move or rotate the catheter to visualize the light movement inside the sinus. After confirming the proper placement of the balloon catheter the surgeon connects the inflation port 154 of the hub 150 to the inflation device. The balloon is inflated to nine atmospheres (range 1 to 30 atmospheres) for the desired time of 60 seconds (range 1 second to 5 minutes). The balloon catheter is then deflated. A second inflation or more inflations can be performed if needed. The balloon catheter can be withdrawn to allow inspection of the ostium or surgical opening if desired. It can then be reinserted if needed for additional inflations. Further, the reinforcing rod can be removed and suction or irrigation performed through the tube 130 if needed.

In some cases the surgeon must push the middle turbinated medially with a periosteal elevator or other instrument to create enough space to place the shaper rod and subsequently the balloon catheter. In some cases part of the middle turbinate must be excised to create sufficient space to place the shaper rod and or balloon catheter.

Figure 14:
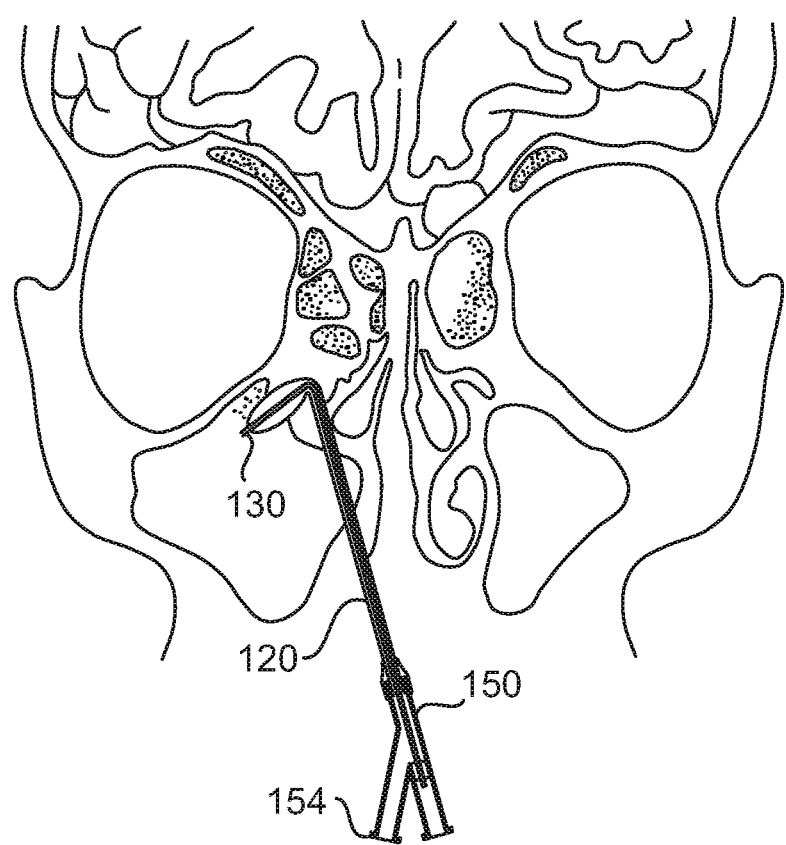
FIG. 14 is a diagrammatical illustration of the use of the tool in a maxillary sinus opening dilatation procedure.
Figure 15:
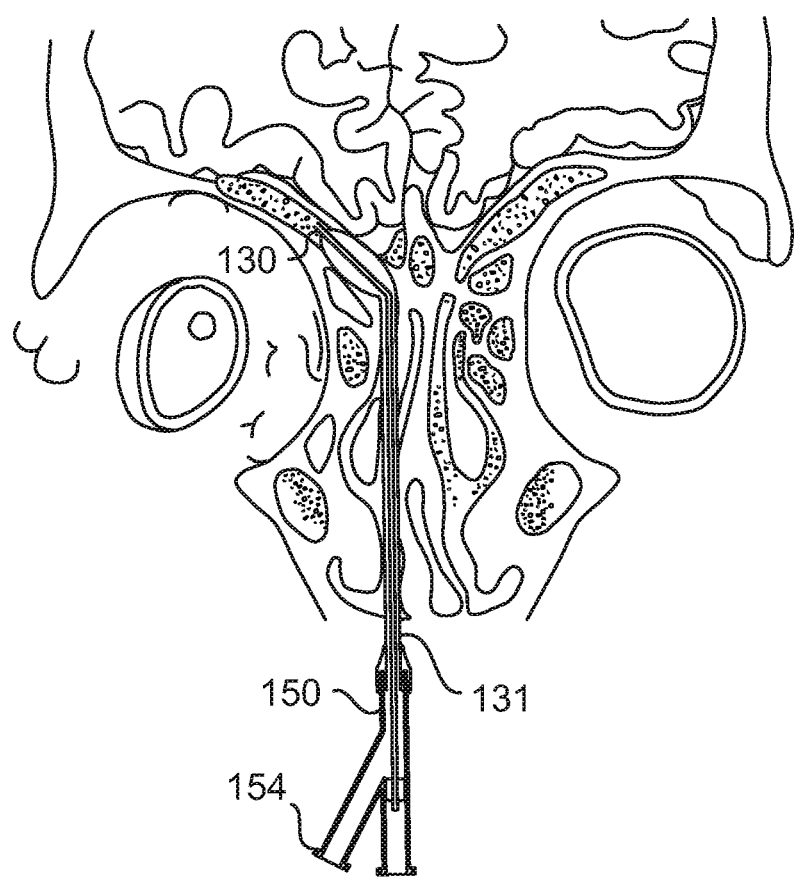
FIG. 15 is a diagrammatical illustration of the use of the tool in a frontal sinus opening dilatation procedure.

With respect to the Frontal sinus as shown in FIG. 14:

The surgeon may first insert a shaping rod into the frontal sinus. The surgeon bends the shaping rod to the desired shape to enter the frontal recess and nasofrontal duct. The surgeon then shapes the tube to the same shape as the shaping rod. Alternatively the physician shapes the tube of the balloon catheter without the shaping rod. The shape is usually a gentle curve for the frontal sinus but may be more acute or larger. He or she then inserts the balloon catheter 131 with reinforcing rod (and LED or other light type in some embodiments) through the stenotic nasofrontal duct or frontal recess or surgically prepared opening in the nasofrontal duct or frontal recess into the sinus cavity. The frontal recess and or frontonasal duct may be entered without other surgical procedures needed. However, in some cases a partial or complete ethmoidectomy is performed first. In some cases the uncinate process is removed first. In some cases a partial or complete middle turbinectomy is performed first. These procedures are needed in some cases to gain access to the frontal recess or nasofrontal duct. The location is confirmed by visualization of the LED or other light illuminating the frontal sinus. In some cases the surgeon may move or rotate the catheter to visualize the light movement inside the frontal sinus. After confirming the proper placement of the balloon catheter the surgeon connects the inflation port 154 of the hub 150 to the inflation device. The balloon is inflated for the desired time to nine atmospheres (range one to thirty atmospheres) for (1 second to 5 minutes, ideally 60 seconds). The balloon catheter is then deflated. A second inflation or more inflations can be performed if needed. The balloon catheter can be withdrawn to allow inspection of the ostium or surgical opening if desired. It can then be reinserted if needed for additional inflations. Further, the reinforcing rod can be removed and suction or irrigation performed through the tube 130 if needed.

The proper angle of the balloon section of the catheter relative to the remainder of the catheter body can be determined by using a small shaper rod that the surgeon bends and places into the ostium or surgically prepared opening to determine the needed shape. Alternatively a set of shape rods may be available. The surgeon uses these to determine the which angle is appropriate.

In another embodiment the shaper rods may be made to allow a fiberoptic cable with a LED or other light on the end inside the lumen. The appropriate shaper rod with light may then be placed through the sinus ostium, surgically prepared opening or in the sinus recess. The light illuminates the sinus to demonstrate that it is in the proper location. The shaper rod is then removed. The tube is then shaped or bent by the surgeon into the desired shape as demonstrated by the chosen shaper rod. The shaper rod may also be part of a set of preshaped rods. The surgeon picks the rod that is best for the insertion into the sinus and then bends the tube into the desired shaped. A special device can be used to aid in bending the tube. The shaper rod may in another embodiment have a lumen to hold a fiberoptic cable with LED or other light on its distal end. This aids in determining if the shaper rod has penetrated the sinus ostium or prepared surgical opening and entered the sinus without a true passage.

While the preferred embodiment of the invention has been described, modifications can be made and other embodiments may be devised without departing from the spirit of the invention and the scope of the appended claims.

What is claimed is:

1. A balloon catheter which comprises:
   an oblong probe which comprises:
      an elongated substantially cylindrical hollow metallic body having a first outer diameter and terminating at a distal extremity and an opposite proximal extremity;
      said body being made from a hard, semirigid, metallic first material;
      a collar bonded to a portion of said body near said proximal extremity;
      said collar being made from a hard, semirigid metallic second material;
      said collar having an outer peripheral surface having a second diameter greater than said first outer diameter;
      a hand graspable hub comprising a second non-metallic rigid material, said hub being secured to said outer peripheral surface along a hub/collar interfacing bond;
   a flexible sheath coaxially engaged by said body;
   wherein said sheath comprises:
      a proximal end portion secured to said hub; and,
      a distal end portion comprising a balloon structure;
   wherein said body has an axial lumen extending from a proximal opening to a distal port; and,
   wherein said hub comprises:
      a first connector leading to a first passageway in fluid communication with said distal port; and,
      a second connector leading to a second passageway in fluid communication with said balloon structure.

2. The device of claim 1, wherein said hub/collar interfacing bond comprises an interface layer contacting said collar and said hub, and wherein said interfacing bond further comprises a proximal bead axially bearing against said collar.

3. The device of claim 1, wherein said hub/collar interfacing bond is capable of withstanding an axial sheer load in excess of 10 Newtons.

4. The device of claim 1, wherein said outer peripheral surface comprises a surface area increasing structure, and wherein said surface area increasing structure comprises a bearing surface having an axial component.

5. The device of claim 1, wherein said outer peripheral surface of said collar is shaped to have a plurality of radial irregularities.

6. The device of claim 1, wherein said second diameter is at least twice as large as said first diameter.

7. The device of claim 1, wherein said sheath has an axial length shorter than an axial length of said body.

8. The device of claim 1, wherein said sheath is shaped and dimensioned to allow for a gap between an outer surface of said body and an inner surface of said sheath.

9. The device of claim 1, wherein said body further comprises:
   said distal extremity being blunted; and,
   said body having a total length between approximately 4 and 50 centimeters and an outer diameter between 0.125 and 5.0 millimeters.

10. The device of claim 1, wherein said first material is taken from a group consisting of: stainless steel, bronze, silver, aluminum, titanium, brass, and alloys thereof.

11. The device of claim 1, wherein said probe has a maximum cross-sectional dimension of between about 1.0 millimeter and 4.0 millimeters.

12. The device of claim 11, which further comprises:
   an elongated reinforcing rod shaped and dimensioned to be inserted into said lumen, and
   wherein said reinforcing rod is further shaped to have a semicircular cross-section, thereby forming an axial groove extending an entire length of said rod; said groove being sized to accommodate passage of a fiberoptic cable therethrough.

13. A method for dilating a small, tight opening through human tissue into the nasal cavity which comprises the steps of:
   inserting the device of claim 1 toward a small, tight opening through human tissue into the nasal cavity;
   pushing the device through said opening until said balloon structure engages said opening;
   wherein said pushing comprises applying an axial force in excess of 10 Newtons to said hub; and,
   inflating said balloon structure.

14. The method of claim 13, wherein said opening consists of an opening selected from the group consisting of a lacrimal opening, an ostium or surgically prepared opening in a sinus selected from the group consisting of the sphenoid sinus, the maxillary sinus, and the frontal sinus.

15. The method of claim 13, which further comprises plastically deforming said device prior to said inserting.

16. The method of claim 13, which further comprises engaging a fiberoptic cable through an axial groove in a reinforcing rod inserted into said axial lumen.

17. The method of claim 13, which further comprises injecting an irrigation or tracer fluid through said device while said device is engaged in said opening; and, suctioning material through said device while said device is engaged in said opening.

18. A device for transnasally dilating a small, tight opening through human tissue into the nasal cavity, said device comprising:
   a tubular metallic body having a proximal extremity, a proximal segment, a distal extremity, and a distal segment and a central lumen;
   a reinforcing rod element shaped to penetrate said lumen;
   a flexible sheath coaxially engaged by said body;
   an inflatable member formed on said sheath proximate to said distal segment;
   said inflatable member being capable of dilating said opening;
   a hand-graspable plastic hub;
   a metallic collar bonded to said proximal segment;
   said hub being secured to said collar;

wherein said sheath comprises:
   a proximal end portion secured to said hub; and,
   said proximal end portion separating said hub from said tubular metallic body;
wherein said tubular body lacks sufficient stiffness and column strength in absence of said reinforcing rod element inserted through said central lumen, to enable said inflatable member, when said inflatable member is deflated, to be inserted transnasally through the naris and into a nasal cavity and subsequently pushed through forces applied on said proximal segment into said opening;
and wherein said tubular body has sufficient stiffness and column strength while said reinforcing rod element is inserted through said central lumen, to enable said inflatable member, when said inflatable member is deflated, to be inserted transnasally through the naris and into a nasal cavity and subsequently pushed through forces applied on said proximal segment into said opening; and,
wherein said distal end is separated from said proximal end a distance sufficient to allow said proximal end to remain outside the nasal cavity while said inflatable member is being pushed into said opening.

* * * * *